(12) United States Patent
Ok et al.

(10) Patent No.: US 7,928,408 B2
(45) Date of Patent: Apr. 19, 2011

(54) MULTI-CHANNEL FLUORESCENCE MEASURING OPTICAL SYSTEM AND MULTI-CHANNEL FLUORESCENCE SAMPLE ANALYZER

(75) Inventors: Gyeong-sik Ok, Busan-si (KR); Su-hyeon Kim, Seoul (KR); Jin-tae Kim, Hwaseong-si (KR); Kwang-wook Oh, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 278 days.

(21) Appl. No.: 11/345,262

(22) Filed: Feb. 1, 2006

(65) Prior Publication Data

US 2006/0202133 A1 Sep. 14, 2006

(30) Foreign Application Priority Data

Feb. 3, 2005 (KR) .................. 10-2005-0010186

(51) Int. Cl.
*G01N 21/64* (2006.01)
(52) U.S. Cl. ................................... 250/458.1
(58) Field of Classification Search ............... 250/458.1, 250/461.1, 461.2, 459.1; 356/318, 417
See application file for complete search history.

(56) References Cited

U.S. PATENT DOCUMENTS

| | | | | |
|---|---|---|---|---|
| 4,967,192 A * | 10/1990 | Hirane et al. | ................. | 345/211 |
| 5,418,371 A * | 5/1995 | Aslund et al. | ............... | 250/458.1 |
| 6,166,804 A * | 12/2000 | Potyrailo et al. | .............. | 356/318 |
| 6,592,733 B1 * | 7/2003 | Foley et al. | .................. | 204/603 |
| 7,170,597 B1 * | 1/2007 | Hooper et al. | ................ | 356/317 |
| 2001/0021018 A1 * | 9/2001 | Basiji et al. | .................... | 356/326 |
| 2002/0113213 A1 * | 8/2002 | Amirkhanian et al. | .... | 250/458.1 |
| 2004/0017150 A1 * | 1/2004 | Fricke et al. | .................. | 313/501 |
| 2004/0125372 A1 | 7/2004 | Walla et al. | .................... | 356/318 |
| 2005/0157299 A1 * | 7/2005 | Heffelfinger | .................. | 356/417 |

FOREIGN PATENT DOCUMENTS

| | | |
|---|---|---|
| CN | 1132558 A | 10/1996 |
| GB | 2 315 130 A | 1/1998 |
| GB | 2 351 556 A | 1/2001 |
| JP | 08-105834 A | 4/1996 |
| JP | 08105834 A | 4/1996 |
| JP | 09-288237 A | 11/1997 |
| JP | 10-281994 A | 10/1998 |
| JP | 2002-195949 A | 7/2002 |

(Continued)

OTHER PUBLICATIONS

European Search Report; EP 06 00 0070; Dated: Apr. 19, 2006.

(Continued)

*Primary Examiner* — David P Porta
*Assistant Examiner* — Kiho Kim
(74) *Attorney, Agent, or Firm* — Cantor Colburn LLP

(57) ABSTRACT

A multi-channel fluorescence measuring optical system and a multi-channel fluorescence sample analyzer using the optical system are provided. The multi-channel fluorescence measuring optical system, which irradiates light onto a plurality of sample channels and detecting fluorescence radiated from samples, includes: a light source; an integrator for giving the light irradiated from the light source a uniform intensity distribution; a sample holder having a plurality of sample channels on which the samples are mounted, wherein the samples are exited by the light emitted from the integrator; and a beam splitter between the integrator and the sample holder for dividing the incident light in a predetermined ratio. Since the light intensities of fluorescence images are detected using optical fiber bundles and photodiodes, the manufacturing cost can be greatly reduced, and the optical system can be miniaturized.

14 Claims, 6 Drawing Sheets

FOREIGN PATENT DOCUMENTS

| | | | |
|---|---|---|---|
| JP | 2003-028866 A | 1/2003 | |
| JP | 2005526254 A | 9/2005 | |
| KR | 10-2000-0044171 A | 7/2000 | |
| KR | 10-2004-0041945 A | 5/2004 | |
| WO | WO 99/42817 | 8/1999 | |
| WO | 0101112 A1 | 1/2001 | |
| WO | WO-01/01112 A1 | * | 1/2001 |
| WO | 03/098279 A2 | 11/2003 | |
| WO | 03098279 A2 | 11/2003 | |
| WO | WO 2004/038350 A1 | 5/2004 | |
| WO | 2004/088291 A1 | 10/2004 | |
| WO | 2004088291 A1 | 10/2004 | |
| WO | WO 2005/003837 A1 | 1/2005 | |

OTHER PUBLICATIONS

"Fluorescence Measurements on Nanotiter Plates"; Authors: M. Hessling, J. Ihlemann and G Marowsky; Review of Scientific Instruments, vol. 71., No. 5, May 2000.

Blom, H., et al. "Parallel Fluorescence Detection of Single Biomolecules in Microarrays by a Diffractive-Optical-Designed 2×2 Fan-Out Element," Applied Optics, vol. 41, pp. 3336-3342 (2002).

Korean Intellectual Property Office, Notice to Submit Response dated Jun. 7, 2006.

Hessling, M., et al., "Fluorescence Measurements on Nanotiter Plates," Review of Scientific Instruments, vol. 21, No. 5, pp. 2201-2105 (2000).

European Patent Office, European Search Report, Date of Completion: Jun. 16, 2006.

European Search Report; EP0701773; Aug. 16, 2007.

Fluorescence measurements on nanotiter plates; M Hessling, J. Ihlemann, G. Marowsky; Review of Scientific Instruments, vol. 71, No. 5; May 2000.

CN OA; Chinese patent Application N. 200610005877.5; Text of the Second Office Action; Sep. 11, 2009.

Office Action issued by the Japanese Patent Office on Mar. 31, 2010; Patent Application No. 2006-011741.

M.Hessling, et al., Fluorescence measurements on nanotiter plates, Review of Scientific Instruments, May 2000, vol. 71/No. 5 p. 2201-2205.

Chinese Patent Office Office Action dated Jul. 2, 2010; Chinese Patent Application No. 200610005877.5.

Notice of Preliminary Reexamination—Japanese Application No. 2010-17048 dated Oct. 26, 2010; citing JP 1998-281994.

* cited by examiner

MULTI-CHANNEL FLUORESCENCE MEASURING OPTICAL SYSTEM AND MULTI-CHANNEL FLUORESCENCE SAMPLE ANALYZER

CROSS-REFERENCE TO RELATED PATENT APPLICATION

This application claims the benefit of Korean Patent Application No. 10-2005-0010186, filed on Feb. 3, 2005, in the Korean Intellectual Property Office, the disclosure of which is incorporated herein in its entirety by reference.

BACKGROUND OF THE INVENTION

1. Field of the Invention

The present invention relates to a multi-channel fluorescence measuring optical system and a multi-channel fluorescence sample analyzer, and more particularly, to a small, cheap multi-channel fluorescence measuring optical system which can rapidly detect fluorescence samples contained in a multi-channel sample holder having several micro-fluidic channels using one optical system, and a multi-channel fluorescence sample analyzer using the optical system.

2. Description of the Related Art

A widely known method of analyzing a sample is to irradiate the sample with a specific wavelength of light and detect the spectrum of light emitted from the sample. For example, DNA concentration is measured by labeling the DNA base with a fluorescent dye and then analyzing the intensity of fluorescence light emitted from the dye.

FIG. 1 illustrates the principle of a sample analyzer which uses general fluorescence analysis. A conventional fluorescence analyzer 100 includes an illuminating unit 110 for irradiating light onto a sample 130, and a detecting unit 120 for detecting fluorescence light emitted from the sample 130. The illuminating unit 110 includes a light source 112, a dichroic mirror 114, and an objective lens 115. The sample 130 is mounted on a sample holder 117. The detecting unit 120 includes a light detector 125, such as a photo multiplier tube (PMT) or photodiode, and a filter 121 for passing only a specific wavelength of light.

The light source 112 can be a halogen lamp, an LED, or a laser. The light emitted from the light source 112 is reflected by the dichroic mirror 114 and strikes the sample 130 on the sample holder 117. The fluorescence light emitted from the sample 130 enters the detecting unit 120 through the dichroic mirror 114. The filter 121 receives the light entering the detecting unit 120 and passes only a specific wavelength, and the light detector 125 detects the intensity of the light from the filter.

Recently, a multi-channel sample analyzer has been developed, to increase the throughput of the sample analysis and rapidly measure the sample. The multi-channel sample analyzer can analyze several samples at once, and can be designed either to simultaneously measure a plurality of samples using a plurality of detecting units, or to sequentially measure a plurality of samples using only one detecting unit.

Apparatuses for simultaneously measuring a plurality of samples using a plurality of detecting units include an apparatus using one detecting unit for each sample (Cepheid Smart Cycler ®), an apparatus in which several samples are simultaneously irradiated by a large one light source, and the fluorescence light emitted from all the samples is measured using one CCD (ABI Prism 7000®, BioRad iCycler®). However, when using as many detecting units as there are samples, the same number of photodetectors, filters, etc., as the samples are required, thereby increasing the volume and the manufacturing cost of the apparatus. Further, when using a CCD detector, only one filter wheel may be used. However, since the highly sensitive CCD needed for fluorescence analysis is expensive, the manufacturing cost of the multi-channel sample analyzer is increased, and thus the analyzer using the CCD detector is not suitable for a small analyzer. Also, in order to perform multi-channel analysis using several wavelengths of light, a rotating filter wheel 143 is generally placed between the sample holder 145 and the CCD 140. However, due to the limit of the frame rate (the number of frame captures per second), the speed of the filter wheel 143 is limited, and thus the time for measuring several wavelengths cannot be further reduced.

Also, the apparatus for sequentially measuring several samples using one detecting unit mounts a plurality of samples on the sample holder and measures the samples by scanning them. The rotating filter wheel is required for multi-color analysis on several wavelengths for one sample, and there is a limit to the multi-channel measuring speed as mentioned above. Also, since the actual measuring time is obtained by multiplying the scanning time of the sample with the filter wheel rotating time, the measuring time is unacceptably long. Also, since a separate device is needed for scanning the samples, the analyzer can not be made small enough.

Particularly, a micro polymerase chain reaction (PCR) using a silicon substrate, which can rapidly control temperature and quickly amplify a very small amount of DNA, can be applied for miniaturization of the PCR equipment, because micro-fluidic channels containing a plurality of samples can be easily formed in a small area of a substrate. However, it is difficult to miniaturize the PCR equipment without miniaturizing the optical system as well. Accordingly, a small optical system must be developed to detect the fluorescence from several micro-fluidic channels.

SUMMARY OF THE INVENTION

The present invention provides a small, cheap multi-channel fluorescence measuring optical system which can rapidly detect fluorescence samples contained in a multi-channel sample holder having a plurality of micro-fluoric paths, and a multi-channel fluorescence sample analyzer using the optical system, The present invention also provides a small, high-speed optical system which can perform multi-channel, multi-wavelength fluorescence measurements at a high speed, and a sample analyzer using the optical system.

According to an aspect of the present invention, there is provided a multi-channel fluorescence measuring optical system for irradiating light onto a plurality of sample channels and detecting fluorescence radiated from samples, comprising: a light source; an integrator for making the light irradiated from the light source have a uniform intensity distribution; a sample holder having a plurality of sample channels on which the samples are mounted, wherein the samples fluorescently react to the light emitted from the integrator; and a beam splitter between the integrator and the sample holder for dividing the incident light in a predetermined ratio.

The light source may be an LED or a LD.

The integrator may be any one of a light tunnel, a light pipe, a diffuser and a fly's eye lens.

A first filter may be provided between the light source and the integrator.

The light source may include an LED array or a LD array emitting a plurality of wavelengths of light to enable multi-wavelength fluorescence measurement.

The LED array or the LD array may be selectively turned on/off according to the wavelength of the light.

According to another aspect of the present invention, there is provided a multi-channel fluorescence measuring optical system for irradiating light onto a plurality of sample channels and detecting fluorescence radiated from samples to measure the multi-wavelength fluorescence, comprising: a plurality of light sources; a plurality of dichroic filters arranged on the path of the light irradiated from the plurality of light sources and transmitting or reflecting incident light according to the wavelength of the light to direct the light traveling along different optical paths toward one direction; an integrator for making the light passing through the plurality of dichroic filters have a uniform intensity distribution; a sample holder having a plurality of sample channels on which the samples are mounted, wherein the samples are excited by the light emitted from the integrator; and a beam splitter between the integrator and the sample holder for dividing the incident light in a predetermined ratio.

The sample holder may have a plurality of micro-fluidic channels formed in a semiconductor substrate, and a sample chamber which collects the samples flowing in the micro-fluidic channels.

According to still another aspect of the present invention, there is provided a multi-channel fluorescence sample analyzer for irradiating light onto a plurality of sample channels and detecting fluorescence radiated from samples to analyze the samples, comprising: a light source; an integrator for making the light irradiated from the light source have a uniform intensity distribution; a sample holder having a plurality of sample channels on which the samples are mounted, wherein the samples are excited by the light emitted from the integrator; a beam splitter between the integrator and the sample holder for dividing the incident light in a predetermined ratio; and a light detecting unit for detecting fluorescence from the samples through the beam splitter, wherein fluorescence images of the samples in the plurality of sample channels are detected as fluorescence intensities in the light detecting unit.

The light detecting unit may have optical fiber bundles corresponding to the sample channels, and photodiodes which face the optical fiber bundles such that the fluorescence images emitted from the sample channels through the optical fiber bundles may be detected.

According to yet another aspect of the present invention, there is provided a multi-channel fluorescence sample analyzer for irradiating light onto a plurality of sample channels and detecting fluorescence radiated from samples to analyze the samples, comprising: a plurality of light sources; a plurality of dichroic filters on the path of the light irradiated from the plurality of light sources, for transmitting or reflecting incident light according to the wavelength of the light to direct the light traveling along different optical paths toward one direction; an integrator for making the light passing through the plurality of dichroic filters have a uniform intensity distribution; a sample holder having the plurality of sample channels on which the samples are mounted, wherein the samples fluorescently react to the light emitted from the integrator; and a beam splitter between the integrator and the sample holder for dividing the incident light in a predetermined ratio, wherein fluorescence images generated by uniformly irradiating the light onto the plurality of sample channels are detected as the fluorescent intensities of the wavelengths of light in the light detecting unit.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
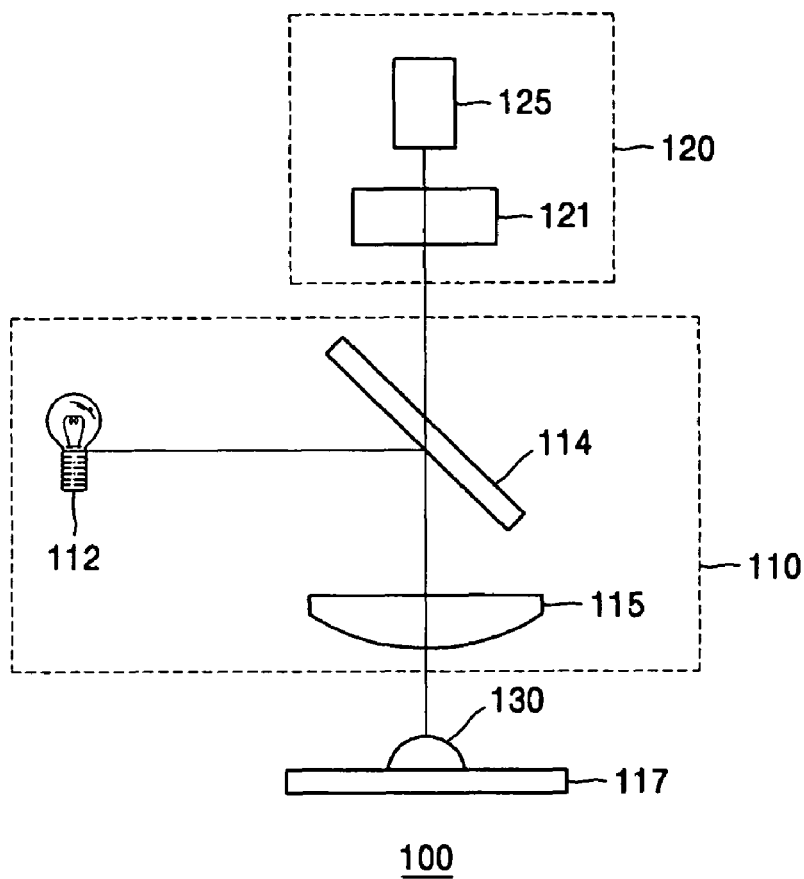
FIG. 1 schematically illustrates a conventional sample analyzer.
Figure 2:
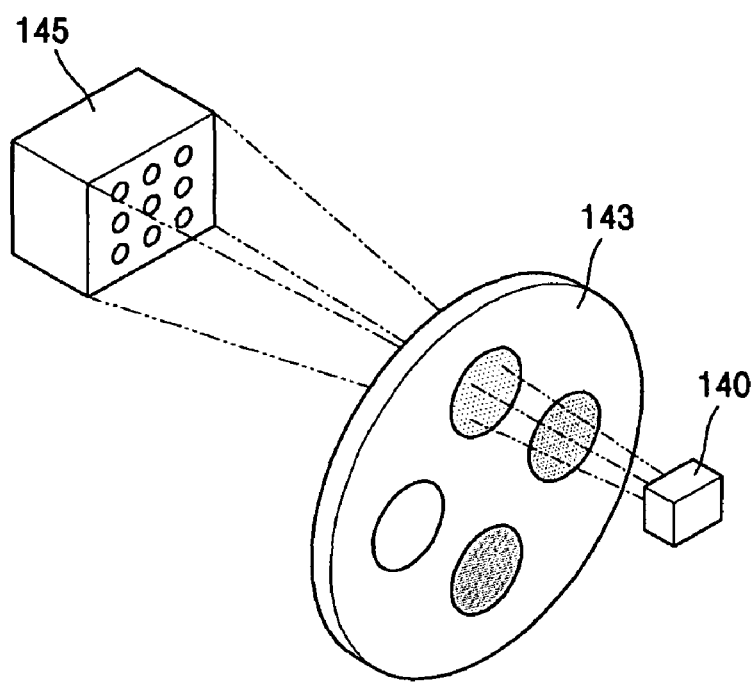
FIG. 2 illustrates an example of a conventional sample analyzer having a rotating filter wheel between a sample holder and a charge-coupled device (CCD)
Figure 3:
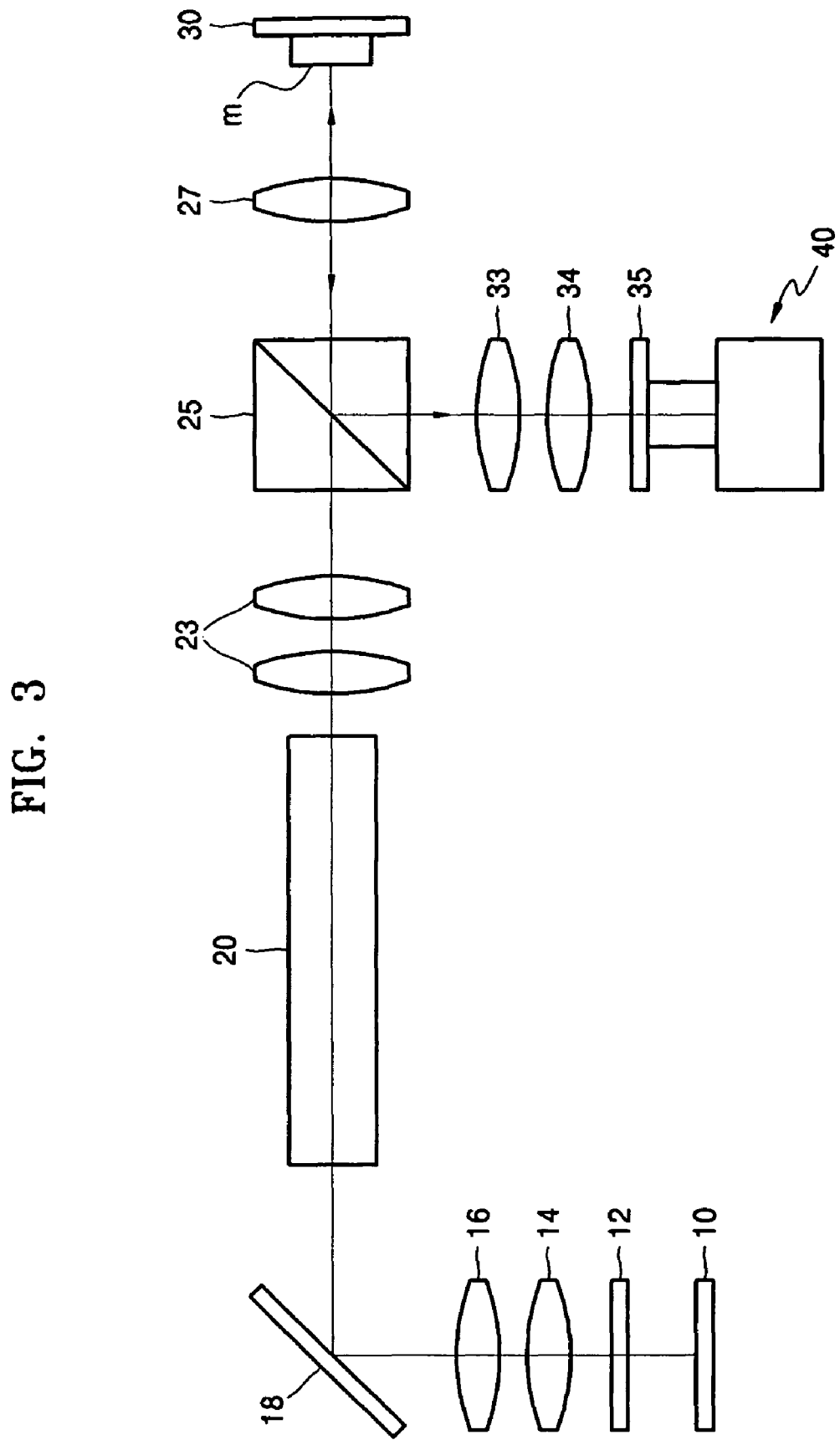
FIG. 3 illustrates a multi-channel fluorescence sample analyzer according to an exemplary embodiment of the present invention.

Referring to FIG. 3, a multi-channel fluorescence measuring optical system according to an embodiment of the present invention includes a light source 10, an integrator 20 for making the light from the light source have a uniform intensity distribution, a sample holder 30 for mounting at least one sample (m) which reacts to the light passing through the integrator 20, and a light detecting unit 40 for detecting the fluorescence emitted from the sample (m). A beam splitter 25 is provided on the optical path between the integrator 20 and the sample holder 30, for transmitting a portion of the incident light and reflecting the other to divide the incident light in a predetermined ratio. A portion of the light transmitted through the integrator 20 is transmitted through the beam splitter 25 to strike the sample (m), and the rest of the light is reflected at the beam splitter.

The fluorescence emitted from the sample (m) is reflected by the beam splitter 25 and directed to the light detecting unit 40.

The light source 10 may be a light emitting element emitting light having a predetermined wavelength, such as an LED or a LD. The LED is preferably a high brightness LED. The LED lasts longer and generates less heat than a lamp. The integrator 20 serves as a surface light source for equalizing the intensity of the light emitted from the light source 10, and may be, for example, a light tunnel, a light pipe, a diffuser or a fly's eye lens.

At least one condenser lens for condensing the incident light may be provided on the optical path between the light source 10 and the integrator 20, and a first filter 12 for improving the wavelength characteristic of the light may also be provided. A first and second condenser lens 14 and 16 are provided between the first filter 12 and the integrator 20. Also, a reflecting mirror 18 for changing the path of the light passing through the second condenser lens 16 may be included. The reflecting mirror 18 is optional depending on the structure of the optical system. That is, the reflecting mirror 18 may be optionally used to change the arrangement of the optical system in a vertical or horizontal direction.

Figure 4A:
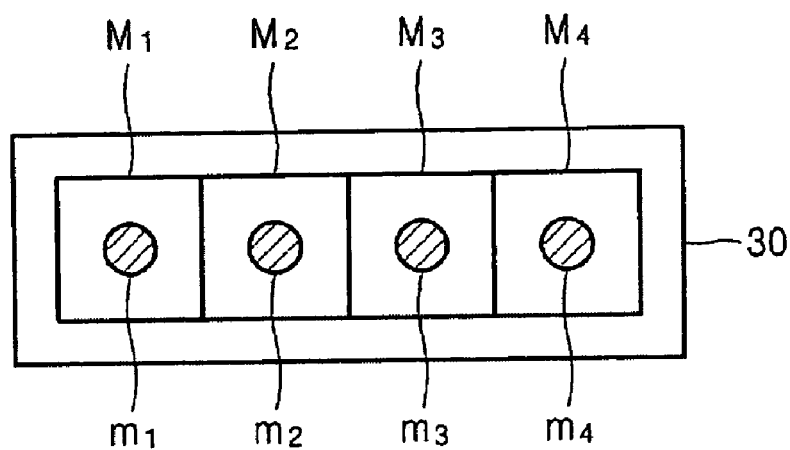
FIG. 4A is a detailed view of an example of a sample holder included in the multi-channel sample analyzer in FIG. 3.
Figure 4B:
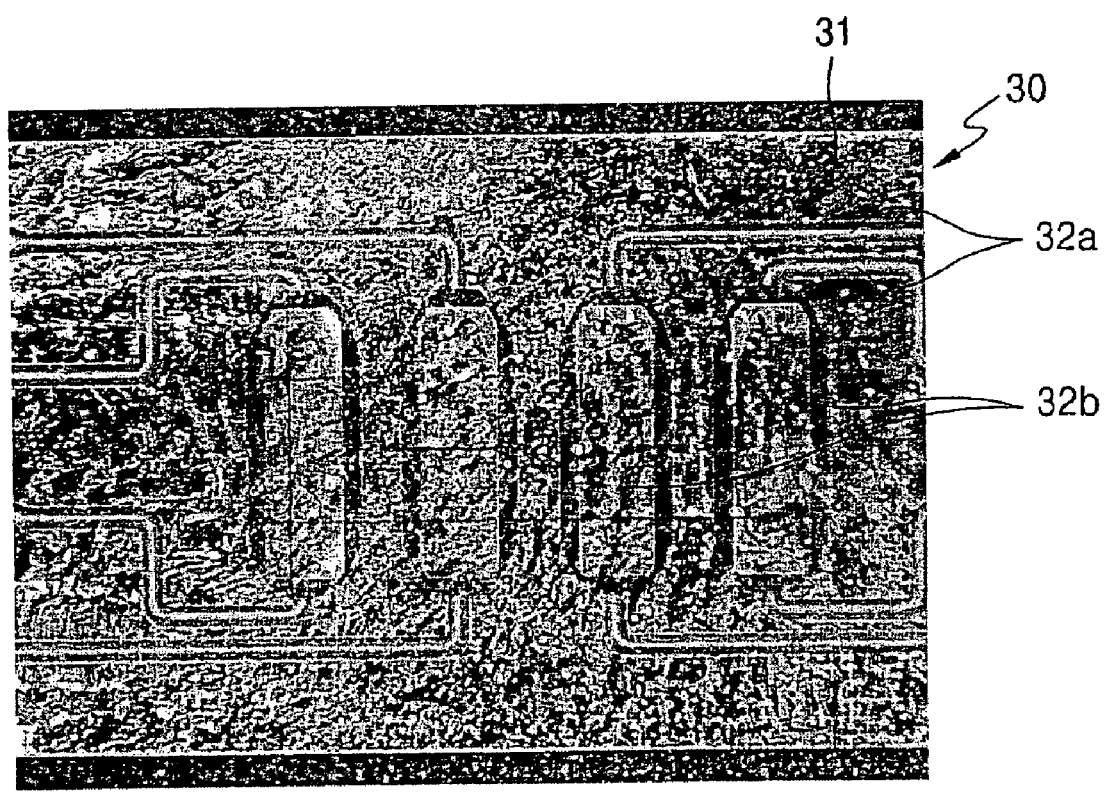
FIG. 4B is a photograph of the sample holder included in the multi-channel sample analyzer in FIG. 3.

The light passing through the integrator 20 has a surface light distribution having a uniform intensity, and is incident to the sample (m) through the beam splitter 25. A relay lens 23 is provided on the optical path between the integrator 20 and the beam splitter 25, and a third condenser lens 27 may be further provided between the beam splitter 25 and the sample holder 30. The sample holder 30 is preferably composed of a plurality of micro-fluidic channels on which a plurality of samples are mounted. The sample is mixed with fluorescent material and, if light is irradiated onto the sample, light is emitted from the fluorescent material. As shown in FIG. 4A, the sample holder 30 includes, for example, a first sample channel M1, a second sample channel M2, a third sample channel M3, and a fourth sample channel M4, and the samples m1; m2, m3 and m4 are mixed with the fluorescent material and mounted on the sample holder. The multi-channel sample holder of the present invention may have various structures. FIG. 4B shows a picture of the multi-channel sample holder having a plurality of the micro-fluidic channels used in the optical system according to the present invention. The multi-channel sample holder 30 is constructed such that micro-fluidic channels 32a are formed in a silicon substrate 31, and the samples supplied through the micro-fluidic channels 32a are collected in sample chambers 32b.

Figure 4C:
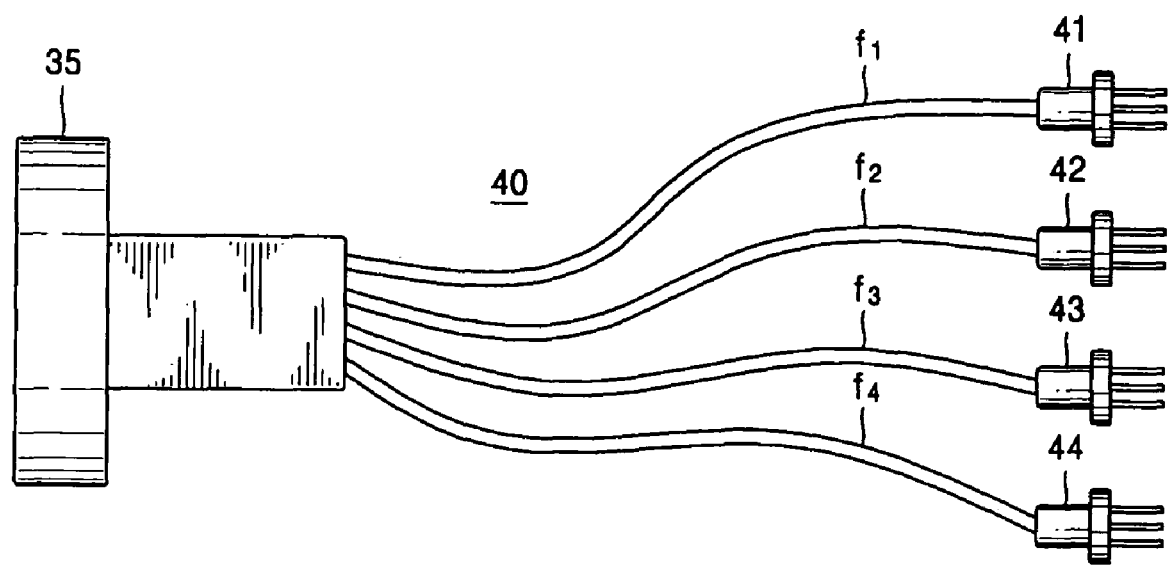
FIG. 4C illustrates an example of a light detecting unit in the multi-channel sample analyzer in FIG. 3.

The fluorescence emitted from the sample is reflected by the beam splitter 25 and directed to the light detecting unit 40. As shown in FIG. 4C, the light detecting unit 40 includes first to fourth optical fiber bundles f1, f2, f3 and f4 which respectively correspond to the first through sample channels M1, M2, M3 and M4, and first to fourth light detectors 41, 42, 43 and 44 which are respectively coupled to the first to fourth optical fiber bundles f1, f2, f3 and f4. The light output from the first to fourth optical fiber bundles f1, f2, f3 and f4 is directly focused onto the first to fourth light detectors 41, 42, 43 and 44. The number of light detectors is equal to the number of sample channels M1, M2, M3 and M4, and the light detectors detect the intensity of fluorescence of the sample in each channel. The light detector is preferably a photodiode. The fluorescence generated by the samples m1, m2, m3 and m4 forms fluorescent images of the samples on the ends of the first to fourth optical fiber bundles f1, f2, f3 and f4. All the optical fibers are divided into as many bundles as there are the sample channels. Ends of the optical fibers at an input end are tied all together into a single bundle, and ends of the optical fibers at an output end are divided into as many bundles as there are the sample channels to allow fluorescent images to respectively enter the photodiodes. Accordingly, the fluorescent image of each sample formed at the distal end of the optical fiber bundle is finally incident to a corresponding photodiode to detect the intensity of the fluorescent image. The cross-section of each bundle of optical fibers functions like a pixel of the CCD. Since the optical fibers are divided into as many optical fiber bundles as there are the sample channels to detect the intensity of light, a pixel binning effect of the CCD is obtained. That is, the fluorescence transmitted through all the optical fibers is divided by the optical fiber bundles so that the intensity of light can be precisely measured by each of the photodiodes.

Fourth and fifth condenser lenses 33 and 34 are arranged on the optical path between the beam splitter 25 and the light detecting unit 40, and a second filter 35 is further included. The first and second filters 12 and 35 selectively divide the wavelength band of the light emitted from the light source 10 to increase the precision of the fluorescence measurement.

The operation for analyzing the fluorescent characteristics of the sample using the analyzer including the above-mentioned multi-channel fluorescent measuring optical system will be described.

The light emitted from the light source 10 is given a uniform square intensity distribution by the integrator 20, and is incident to the beam splitter 25. A portion of the light is transmitted through the beam splitter 25 towards the sample channels M1, M2, M3 and M4. The fluorescence radiated from the sample of the sample channel enters the light detecting unit 40 through the beam splitter 25. The light radiated from the sample channels M1, M2, M3 and M4 is condensed onto the first to fourth light detectors 41, 42, 43 and 44 through the optical fiber bundles f1, f2, f3 and f4, and the light detector detects the intensity of the fluorescence. The intensity of the fluorescence is analyzed to measure the amount of DNA in the sample.

In the present invention, the fluorescence of the plurality of samples in the multiple channels can be simultaneously measured. In general, an apparatus for simultaneously measuring the fluorescence of a plurality of samples in multiple channels includes a large optical system. However, in the present invention, since one optical system which is common to multiple channels is used, the analyzer can be miniaturized and manufactured at a lower cost. Further, by miniaturizing the optical system, a sample analyzer suitable for an ultra small sample holder having a plurality of the micro-fluidic channels can be manufactured. This is realized by forming a surface light source using a light source having low power and low heat output and an integrator and forming a light detecting unit including optical fiber bundles and photodiodes.

Next, an analyzer which can perform multi-channel and multi-wavelength fluorescence measurements using the optical system shown in FIG. 3 will be described.

In order to utilize an internal control factor in PCR, in addition to a primer sample to be detected, or use multiplex PCR which can simultaneously amplify several kinds of DNA in a single experiment, several kinds of DNA in a sample are quantized by incorporating at least two dyes of different colors to the sample and measuring at least two different fluorescence signals. In this case, it is preferable that the optical system is constructed to enable multi-channel and multi-wavelength fluorescence measurement. In order to quantify the different intensities of the fluorescence in a multi-channel and multi-wavelength fluorescence measurement, the transmission band of the filter must be designed according to the maximum fluorescence wavelength band of each dye, and the wavelength of the light source must be designed to induce the maximum fluorescence intensity of each dye.

Figure 5A:
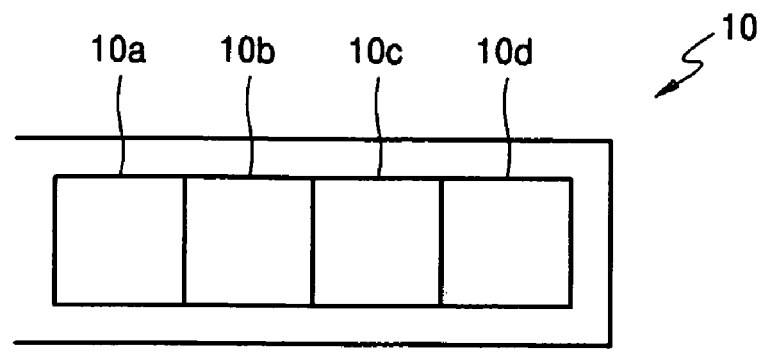
FIG. 5A illustrates an exemplary structure of a light source included in the multi-channel fluorescence measuring optical system in FIG. 3.

As shown in FIG. 5A, the light source 10 may include a plurality of LEDs or LDs 10a, 10b, 10c and 10d for irradiating the plurality of wavelengths of light. Here, an example where the light source 10 is composed of LEDs will be described. For example, the light source 10 includes a first LED array 10a for irradiating a first wavelength of light, a second LED array 10b for 10a for irradiating a second wavelength of light, a third LED array 10c for irradiating a third wavelength of light, and a fourth LED array 10d for irradiating a fourth wavelength of light.

The first to fourth LED arrays 10a, 10b, 10c and 10d can be selectively turned on and off. When using such a light source emitting light having multiple wavelengths, the light detecting unit 40 includes first to fourth optical fiber bundles f11, f12, f13 and f14 which respectively correspond to the first to fourth sample channels, first to fourth light detectors 51, 52, 53 and 54 which face the first to fourth optical fiber bundles f11, f12, f13 and f14, respectively, and a filter wheel 45 between the first to fourth optical fiber bundles f11, f12, f13 and f14 and the first to fourth light detectors 51, 52, 53 and 54. The first to fourth light detectors may be, for example, first to fourth photodiodes.

The filter wheel 45 is constructed in a structure corresponding to the plurality of wavelengths of light emitted from the light source 10. That is, if the light source 10 includes first through fourth wavelength light sources, the filter wheel 45 includes first to fourth filters 45a, 45b, 45c and 45d for filtering the first to fourth wavelength lights so as to measure the fluorescence generated by the sample at the first to fourth wavelengths. The first filter 45a filters the first wavelength light, the second filter 45b filters the second wavelength light, the third filter 45c filters the third wavelength light, and the fourth filter 45d filters the fourth wavelength light. The filter wheel 45 is rotatable.

The filter wheel 45 rotates in synchronization with the ON/OFF operation of the first through fourth wavelength light sources. The filter wheel 45 rotates once whenever each of the first through fourth wavelength light sources is turned on.

The first through fourth wavelengths of light are sequentially irradiated from the light source 10, and the first wavelength light is made uniform by the integrator 20 to be uniformly irradiated onto all the sample channels of the multi-channel sample holder 30. The first channel fluorescence to the fourth channel fluorescence radiated from the sample channels in the multi-channel sample holder 30 are respectively transmitted to the first to fourth optical fiber bundles f11, f12, f13 and f14 through the beam splitter 25. The first channel fluorescence to fourth channel fluorescence transmitted through the first to fourth optical fiber bundles passes through the filter wheel 45. The light emitted from the first to fourth wavelength light source is filtered by the first to fourth filters 45a, 45b, 45c and 45d and the fluorescence radiated from the sample is transmitted through the first to fourth filters 45a, 45b, 45c and 45d.

As the filter wheel 45 rotates, the first channel light to the fourth channel light for the first wavelength of light is filtered by the first filter 45a and is incident on the first to fourth photodiodes 51, 52, 53 and 54. Next, when the second wavelength of light is emitted, the first channel light to the fourth channel light for the second wavelength of light is sequentially filtered by the second filter 45b and is incident on the first to fourth photodiodes, as with the first wavelength of light. Also, the first channel light to the fourth channel light for the third wavelength of light and the fourth wavelength of light are detected. At this time, by quantizing the intensity of light detected by each photodiode in consideration of the wavelength of the incident light and the wavelength of the fluorescence passing through the filter wheel, the fluorescent intensity of the plurality of wavelengths of light in the multi-channels can be rapidly and precisely measured.

Figure 6:
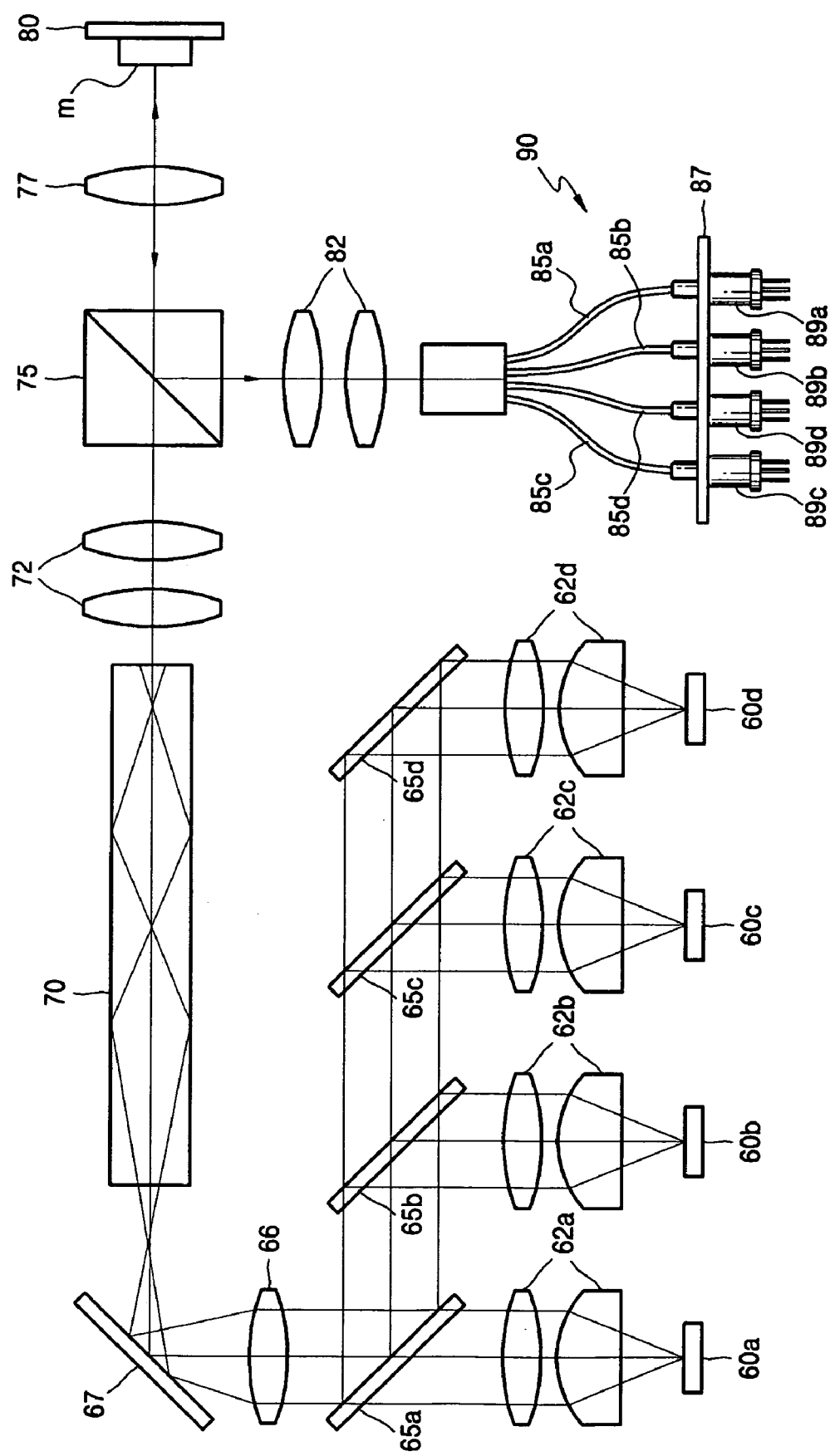
FIG. 6 illustrates a multi-channel sample analyzer according to another embodiment of the present invention.

Next, a fluorescence sample analyzer using an optical system according to another embodiment of the present invention is shown in FIG. 6.

An optical system according to another embodiment of the present invention includes a first light source 60a, a second light source 60b, a third light source 60c, a fourth light source 60d, and an integrator 70 for giving the light emitted from the first to fourth light sources 60a, 60b, 60c and 60d a uniform intensity distribution. A first dichroic filter 65a for transmitting a first wavelength of light and reflecting other light is provided on the optical path between the first light source 60a and the integrator 70. Also, second, third and fourth dichroic filters 65b, 65c and 65d are provided in parallel with the first dichroic filter 65a. The second dichroic filter 65b reflects the second wavelength of light to send it to the first dichroic filter 65a and transmits other light from the second light source 60b. The third dichroic filter 65c reflects the third wavelength of light to send it to the second dichroic filter 65b and transmits other light from the third light source 60c. The fourth dichroic filter 65d reflects the fourth wavelength of light to send it to the third dichroic filter 65c and transmits other light from the fourth light source 60d.

The first to fourth light sources 60a, 60b, 60c and 60d may be white light sources or monochromatic light sources. The monochromatic light source may be an LED or a LD.

The condenser lenses 62a, 62b, 62c and 62d are included between the first light source 60a and the first dichroic filter 65a, between the second light source 60b and the second dichroic filter 65b, between the third light source 60c and the third dichroic filter 65c, and between the fourth light source 60d and the fourth dichroic filter 65d.

In the light from the first light source 60a, the first wavelength of light is transmitted through the first dichroic filter 65a to be directed to the integrator 70, and other light is reflected. In the light from the second light source 60b, the second wavelength of light is reflected from the second dichroic filter 65b to be directed to the first dichroic filter 65a and other light is transmitted. The second wavelength of light is reflected by the first dichroic filter 65a to be directed to the integrator 70.

In the light from third light source 60c, the third wavelength of light is reflected by the third dichroic filter 65c, transmitted through the second dichroic filter 65b, and reflected by the first dichroic filter 65a, to be directed to the integrator 70. In the light from the fourth light source 60d, the fourth wavelength of light is reflected by the fourth dichroic filter 65d, transmitted through the third and second dichroic filters 65c and 65b, and reflected by the first dichroic filter 65a to be directed to the integrator 70. Here, if the fourth light source 60d irradiates the fourth wavelength of light, a reflecting mirror may be included instead of the fourth dichroic filter 65d.

Finally, the light emitted from the first to fourth light sources 60a, 60b, 60c and 60d is directed in any one direction by the first to fourth dichroic filters 65a, 65b, 65c and 65d. A reflecting mirror 67 for changing the optical path to change the optical system arrangement may be further provided on the optical path between the first dichroic filter 65a and the integrator 70. Also, a condenser lens 66 is further provided between the first dichroic filter 65a and the reflecting mirror 67.

The light emitted from the first to fourth light sources 60a, 60b, 60c and 60d is given a uniform intensity distribution by the integrator 70, and a portion of the light is transmitted through the beam splitter 75 to the multi-channel sample holder 80. The integrator 70 serves as a surface light source. A relay lens 72 is provided on the optical path between the integrator 70 and the beam splitter 75, and a condenser lens 77 may be further provided between the beam splitter 75 and the multi-channel sample holder 80.

The multi-channel sample holder 80 includes a plurality of micro-fluidic channels on which a plurality of the samples can be mounted, as mentioned with reference to FIG. 5A.

The fluorescence radiated from the multi-channel sample holder 80 is reflected from the beam splitter 75 onto the light detecting unit 90. A condenser lens 82 is further provided between the beam splitter 75 and the light detecting unit 90. The light detecting unit 90 includes as many optical fiber bundles 85a, 85b, 85c and 85d as there are sample channels in the multi-channel sample holder 80, a filter wheel 87, and light detectors 89a, 89b, 89c and 89d which face the optical fiber bundles 85a, 85b, 85c and 85d, respectively. The light detectors 89a, 89b, 89c and 89d are photodiodes.

Figure 5B:
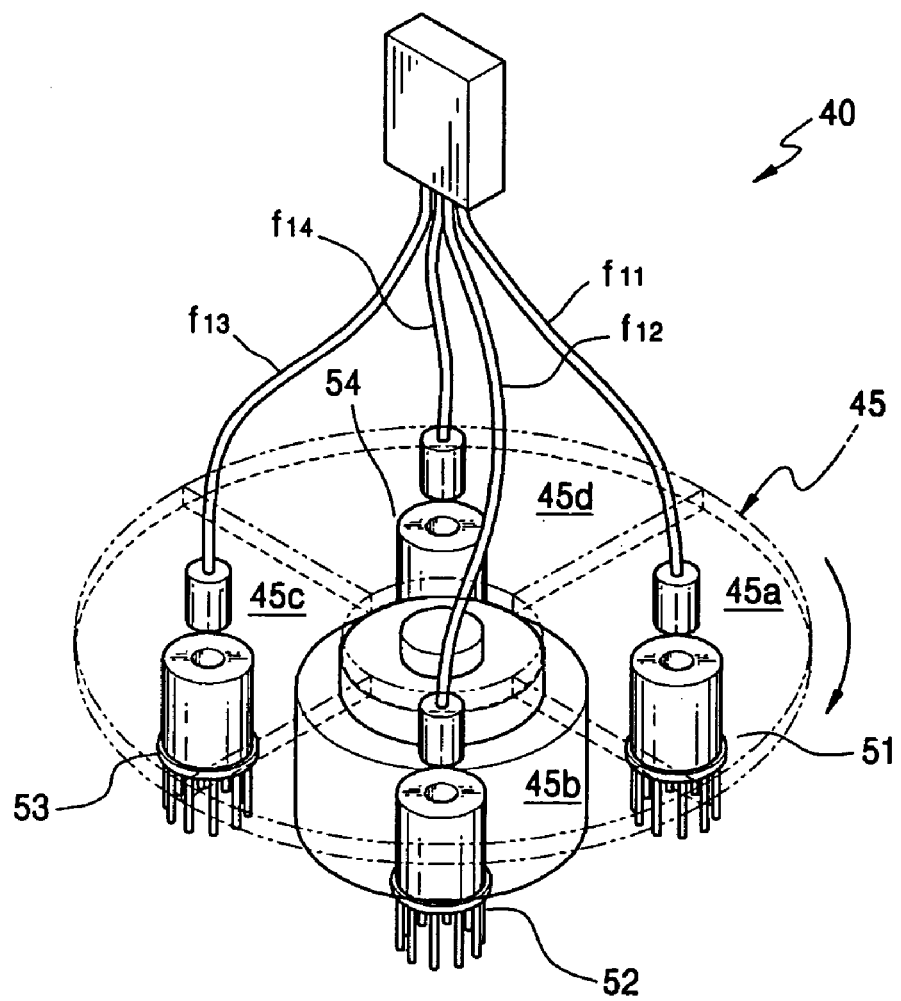
FIG. 5B illustrates another example of the light detecting unit in the multi-channel sample analyzer in FIG. 3.

Since the light detecting unit 90 has the same structure, operation and effect as the light detecting unit 40 described with reference to FIG. 5B, its description will be omitted.

In the current embodiment, a plurality of light sources for multi-wavelength and multi-channel fluorescence measurement and a plurality of dichroic filters which direct the light emitted from the plurality of light sources to travel along a single path are provided.

Accordingly, DNA contained in each sample is quantified by selectively and uniformly irradiating the different wavelengths of light onto the multi-channel sample and detecting the intensity of a fluorescent image for each sample in the light detector through an optical fiber bundle.

As described above, in a multi-channel fluorescence measuring optical system and a sample analyzer using the same according to the present invention, the fluorescence of multi-channel sampled can be measured using a common optical system, thereby miniaturizing the optical system. Also, since the intensity of the fluorescence can be measured using the optical fiber bundled and the photodiodes, the manufacturing cost can be greatly reduced. Also, a small optical system for multi-channel measurement can be provided by forming a surface light source using the optical element having low power and low heat output, such as a LED and an integrator, and a light detecting unit composed of optical fiber bundles and the photodiodes. The small optical system for multi-channel measurement can be used in a sample analyzer including an ultra small multi-channel sample holder having several micro-fluidic channels. Therefore, a portable sample analyzer can be developed, and a plurality of samples can be analyzed using such a multi-channel analyzer.

Further, multi-color fluorescence can be measured by using the light source for irradiating the plurality of wavelengths of light. Particularly, the multi-color fluorescence can be measured using one optical system and thus the optical system can be miniaturized and the manufacturing cost thereof can be greatly reduced. Therefore, a portable multi-channel sample analyzer including the optical system according to the present invention can be realized, and various sample characteristics can be precisely analyzed using multiple wavelengths of light.

Also, when samples contain several kinds of dye, multiple wavelengths of light can be detected using a filter wheel, and thus several kinds of DNA contained in the samples can be simultaneously and rapidly quantified.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A multi-channel fluorescence sample analyzer for irradiating light onto a plurality of sample channels and detecting fluorescence radiated from samples to analyze the samples, comprising:
   a light source;
   an integrator which increases a uniformity of the light irradiated from the light source;
   a sample holder having a plurality of sample channels on which the samples are mounted, wherein the samples are excited by the light emitted from the integrator, and wherein the sample holder is uniformly exposed to the light emitted from the integrator such that each portion of the sample holder receives substantially a same amount of light;
   a beam splitter between the integrator and the sample holder for dividing light incident thereto in a predetermined ratio; and
   a light detecting unit for simultaneously detecting fluorescence from the samples through the beam splitter,
   wherein fluorescence images of the samples in the plurality of sample channels are detected as florescence intensities in the light detecting unit, and the sample holder, the beam splitter and the light detection unit are arranged to transmit light from the plurality of sample channels to the light detection unit along substantially parallel optical paths,
   wherein the light detecting unit has optical fiber bundles corresponding to the sample channels, and photodiodes which face the optical fiber bundles respectively such that the fluorescence images emitted from the sample channels through the optical fiber bundles are detected.

2. The multi-channel fluorescence sample analyzer according to claim 1, wherein the light source is an LED or a LD.

3. The multi-channel fluorescence sample analyzer according to claim 1, wherein the integrator is any one of a light tunnel, a light pipe, a diffuser and a fly's eye lens.

4. The multi-channel fluorescence sample analyzer according to claim 1, wherein a first filter is included between the light source and the integrator.

5. The multi-channel fluorescence sample analyzer according to claim 1, wherein a second filter is provided between the beam splitter and the light detecting unit.

6. The multi-channel fluorescence sample analyzer according to claim 1, wherein the light source includes an LED array or a LD array emitting a plurality of wavelengths of light to enable multi-wavelength fluorescent measurement.

7. The multi-channel fluorescence sample analyzer according to claim 6, wherein the LED array or the LD array is selectively turned on/off according to the wavelength of light.

8. The multi-channel fluorescence sample analyzer according to claim 6, wherein the light detecting unit has optical fiber bundles corresponding to the sample channels, photodiodes which face the optical fiber bundles such that the fluorescence images emitted from the sample channels through the optical fiber bundles are detected, and a filter wheel which is provided between the optical fiber bundles and the photodiodes and filters the plurality of wavelengths of light.

9. The multi-channel fluorescence sample analyzer according to claim 8, wherein the filter wheel rotates once whenever each of the plurality of wavelengths of light is turned on.

10. The multi-channel fluorescence sample analyzer according to claim 1, wherein the sample holder has a plurality of micro-fluidic channels formed in a semiconductor substrate and a sample chamber which collects the samples flowing in the micro-fluidic channels.

11. A multi-channel fluorescence sample analyzer for irradiating light onto a plurality of sample channels and detecting fluorescence radiated from samples to analyze the samples, comprising:
   a plurality of light sources wherein the plurality of light sources includes at least two light sources individually controlled to emit light at different wavelengths from each other;
   a plurality of dichroic filters on the path of the light irradiated from the plurality of light sources, for transmitting or reflecting incident light according to the wavelength of the light to direct the light traveling along different optical paths toward one direction;

an integrator for making the light passing through the plurality of dichroic filters have a uniform intensity distribution;

a sample holder having the plurality of sample channels on which the samples are mounted, wherein the samples are excited by the light emitted from the integrator, and wherein the sample holder is uniformly exposed to the light emitted from the integrator; and a beam splitter between the integrator and the sample holder for dividing light incident thereto in a predetermined ratio, wherein fluorescence images generated by uniformly irradiating the light onto the plurality of sample channels are simultaneously detected as fluorescent intensities in the light detecting unit, and wherein the light detecting unit has optical fiber bundles corresponding to the sample channels, photodiodes which face the optical fiber bundles respectively such that the fluorescence images emitted from the sample channels through the optical fiber bundle are detected, and a filter wheel which is provided between the optical fiber bundles and the photodiodes and filters a plurality of wavelengths of light, and wherein the at least two light sources are controlled such that light having a first wavelength emitted from a first light source of the at least two light sources is emitted at a different time than light having a second wavelength, which is different than the first wavelength, emitted from a second light source of the at least two light sources.

12. The multi-channel fluorescence sample analyzer according to claim 11, wherein the plurality of light sources include an LED or a LD.

13. The multi-channel fluorescence sample analyzer according to claim 11, wherein the integrator is any one of a light tunnel, a light pipe, a diffuser and a fly's eye lens.

14. The multi-channel fluorescence sample analyzer according to claim 11, wherein the filter wheel rotates once whenever a light source of the plurality of light sources which emits light at a different wavelength is turned on.

* * * * *